(12) United States Patent
Hebert et al.

(10) Patent No.: US 6,451,354 B1
(45) Date of Patent: Sep. 17, 2002

(54) NATURAL PRODUCT COMPOSITION FOR DECREASING IGE PRODUCTION AND TREATING SECONDARY ALLERGIC RESPONSES

(75) Inventors: Rolland Hebert, Seattle, WA (US); Edayatimangalam Raja Bhavani Shanmugasundaram; Kalathkal Radha Shanmugasundaram, both of Chennai (IN)

(73) Assignee: Pharma Terra, Inc., Marcer Island, WA (US)

( * ) Notice: Subject to any disclaimer, the term of this patent is extended or adjusted under 35 U.S.C. 154(b) by 0 days.

(21) Appl. No.: 09/696,498

(22) Filed: Oct. 25, 2000

Related U.S. Application Data

(60) Provisional application No. 60/162,038, filed on Oct. 26, 1999.

(51) Int. Cl.⁷ .................. A61K 35/78; A61K 33/10; A61K 33/04; A61K 33/00
(52) U.S. Cl. .................. 424/725; 424/725.1; 424/734; 424/750; 424/756; 424/682; 424/686; 424/687; 424/703; 424/715; 424/680; 514/826; 514/921
(58) Field of Search .................. 424/725, 725.1, 424/734, 750, 756, 680, 682, 686, 687, 703, 715; 514/826, 921

(56) References Cited

U.S. PATENT DOCUMENTS 5,683,698 A * 11/1997 Chavali et al.
6,027,728 A * 2/2000 Yuen

FOREIGN PATENT DOCUMENTS

GB  2314270  * 12/1997

OTHER PUBLICATIONS

Amrita Bindu —A Salt–spice–herbal health food supplement for prevention of Nitrosamine induced depletion of antioxidants. K.R. Shanmusasundaram et al, Journal of Ethnopharmalopy, 42, 1994 pp. 83–93.

Amrita Bindu therapy in diabetic retino path: effect on antioxidant defenses and the disease process. Parthiban et al, Perfusion vol 9, 1996 pp. 280–283.

* cited by examiner

Primary Examiner—Christopher R. Tate

(57) ABSTRACT

A salt-spice-herbal composition known as Amrita Bindu that is clinically useful for reducing IgE production and treating secondary allergic responses is disclosed.

4 Claims, 4 Drawing Sheets

NATURAL PRODUCT COMPOSITION FOR DECREASING IGE PRODUCTION AND TREATING SECONDARY ALLERGIC RESPONSES

This Application claims benefit of Provisional No. 60/162,038 filed Oct. 26, 1999.

FIELD OF THE INVENTION

The present invention relates to compositions and methods for decreasing IgE production and IgE levels in mammalian subjects and treating secondary allergic responses.

BACKGROUND OF THE INVENTION

Allergic reactions include four types, i.e., types I, II, III and IV. The type I (immediate-type, anaphylactic) allergic reaction is triggered by the reaction-relating-factor immunoglobulin E (hereinafter abbreviated as an IgE antibody). The reaction steps can be divided roughly into the following three steps. The first step is a sensitization step involving IgE antibody production and binding of the resulting IgE antibodies to mast cells or basophils. The second step involves degranulation of the mast cells or basophils and release of chemical mediators. The third steps involves onset of effects of the released chemical mediators on the target organs. Thus, the type I allergic reaction against foreign antigens leads to onset of symptoms through the above reaction steps.

Only symptomatic treatments by inhibiting the above second and/or third reaction steps have been carried out to treat allergic diseases. That is, the treatments are carried out by inhibiting the release of chemical mediators accompanying the degranulation and/or by inhibiting allergic reactions induced by the released chemical mediators. These symptomatic treatments have been known to be effective not only in systemic administration of anti-allergic agents but also in their topical administration to the nose, etc. However, the effects of the treatments are limited because the treatments do not inhibit IgF antibody production which is the basic first step of the type I allergic reaction.

As fundamental remedies against the type I allergic reaction, agents inhibiting or modulating the above first step, namely IgE antibody production inhibitors, are being developed.

Type I allergy is an inflammatory response which is elicited as the invasion of foreign agents into the body which results in the release of various enzymes and chemical mediators, such as histamine and leukotrienes, from mast cells and eosinophils, which in turn induce tissue-damaging inflammations. The allergic response, when generalized, can lead to a systemic and often life threatening reaction known as anaphylactic shock.

In pollen allergy for example, symptoms occur preferentially in the nose and eye. In recent years, there has been a rapid increase in the number of patients who complain of the so-called pollinosis symptoms due to pollens of cedar and other allergenic plants, resulting in, for example, allergic conjunctivitis and allergic rhinitis (eye watering, sinus congestion, nasal congestion, sneezing and the like). For the prevention of pollen disease, a prophylactic treatment with antiallergic agents, a symptomatic treatment with antihistamines and steroids, and hyposensitization therapy are generally indicated.

However, there is not available as yet an antiallergic agent effective enough and devoid of nocive side effects as a preventive drug, while the antihistamines and steroids in current use for symptomatic treatment have the problem of side effects.

Conditions in which IgE is elevated:

Atopy provides the hereditary basis for allergic responses. The condition is a congenital hypersensitivity to specific agents, and is usually manifested as bronchial asthma and allergic rhinitis. Atopic dermatitis is an inflammatory disease of the skin which may arise because of a predisposition and which is often characterized by areas of localized itch. It is also known that as the affected area is scratched, the local eruption is aggravated so that the disease runs a chronic course. Moreover, the pruritus associated with atopic dermatitis develops suddenly in many cases and tends to be provoked and intensified by the slightest stimulation.

A variety of treatments have been attempted for atopic dermatitis, but they have proved unsuccessful. The current therapeutic modality for this disease consists of the topical treatment primarily with adrenocorticoids and, as an adjunct therapy, antipruritic agents such as antihistamines. But since these drugs are not without side effects, the advent of a safe and more sure-acting drug for the prevention and treatment of atopic dermatitis has been anticipated.

Patients with bronchial asthma are rapidly increasing in number and present a serious problem everywhere in the world today. Bronchial asthma is an airway disease, the cardinal manifestation of which is respiratory distress due to paroxysmal airway constriction, which is life threatening at times. While many etiologic agents are usually involved in the onset of bronchial asthma, the chief cause is generally believed to be an increased airway responsiveness due to allergic factors associated with inhaled antigens such as cockroaches, ticks, pollens, dust and so on.

For the treatment of bronchial asthma, prophylaxis with antiallergic drugs and symptomatic treatment with beta.-receptor stimulants and steroids are practiced today, but there is no antiallergic drug effective enough as a prophylactic. Further, the problem of side effects has been pointed out frequently with the use of beta.-receptor stimulants and steroids used for symptomatic treatment.

As mentioned earlier, the first step in the pathogenesis of an allergic response is the production of immunoglobulin E (IgE) antibody in response to an allergen. Upon exposure to allergens, the B cells of responsive individuals secrete IgE molecules specific to the allergen. IgE molecules bind to the high affinity IgE receptor present on mast cells and basophils. IgE binding activates the release of a variety of vasoactive mediators that promote allergic and inflammatory responses. Activation occurs whenever two or more high affinity IgE receptors are cross linked via bound IgE molecules that in turn form an aggregate with an allergen molecule.

Such aggregation initiates a biochemical cascade that releases histamine and proteases from cytoplasmic granules and leads to the synthesis of prostaglandins, leukotrienes, cytokines and other effectors of the hypersensitivity response. Mast cells and basophils accumulate at sites of inflammation and, upon activation, secrete hemopoietic growth factors such as granulocyte/macrophage colony-stimulating factor, interleukin-3, and interleukin-6. These factors propagate the inflammatory response by recruiting, priming, and activating inflammatory cells such as neutrophils, macrophages and eosinophils. The activated cells accumulate in areas of ongoing inflammation, tumor invasion, angiogenesis, fibrosis, and thrombosis. The IgE-dependent activation of cells via high affinity IgE receptors results in an inflammatory response directed towards local tissue defense, tissue maintenance and remodeling, and immunoregulation (Gagari, E. et al (1997) Blood 89:2654–2663). Preventing the IgE activation of cells would be an important step in preventing or treating conditions in which elevated IgE levels are a hallmark.

Currently, therapy for treatment of inflammation predominantly involves the use of glucocorticosteroids. Other anti-inflammatory agents are used including cromolyn and nedocromil. Symptomatic treatment with beta-agonists, anticholinergic agents and methyl xanthines are clinically beneficial for the relief of discomfort but fail to stop the underlying inflammatory processes that cause the disease. The frequently used systemic glucocorticosteroids have numerous side effects, including, but not limited to, weight gain, diabetes, hypertension, osteoporosis, cataracts, atherosclerosis, increased susceptibility to infection, increased lipids and cholesterol, and easy bruising. Aerosolized glucocorticosteroids have fewer side effects but can be less potent and have side effects, such as thrush.

Other anti-inflammatory agents, such as cromolyn and nedocromil are much less potent and have fewer side effects. Anti-inflammatory agents that are primarily used as immunosuppressive agents and anticancer agents (i.e., cytoxan, methotrexate and immuran) have also been used to treat inflammation. These agents, however, have serious side effect potential, including, but not limited to, increased susceptibility to infection, liver toxicity, drug-induced lung disease, and bone marrow suppression. Thus, such drugs have found limited clinical use for the treatment of most airway hyperresponsiveness lung diseases. Recently, a new approach to modulating or inhibiting the IgE response has been studied in humans. Anti-IgE monoclonal antibodies have been administered to asthmatic subjects in order to assess their efficacy in the early and late responses to allergen administration by inhalation in asthmatic subjects. The IV administration of such anti-IgE monoclonal antibodies significantly lowered serum IgE levels in 6 of 9 subjects and this resulted in attenuation of early-phase as well as the late-phase response. (The Effect of an Anti-IgE Monoclonal Antibody on the Early and Late Phase Response to Allergen Inhalation in Asthmatic Subjects. Fahy et al, Am J Respir Crit Care Med Vol. 155, pp 1828–1834, 1997. IgE inhibition as a Therapy for Allergic Disease, Jardieu, P and Fick, Robert, Int Arch Allergy Immunol 1999; 118: 112–115.) However, while this study showed that significant clinical response can be obtained using anti-IgE antibodies, the administration of this medication is by intravenous route that can be expensive and uncomfortable for the patients.

SUMMARY OF THE INVENTION

Figure 1:
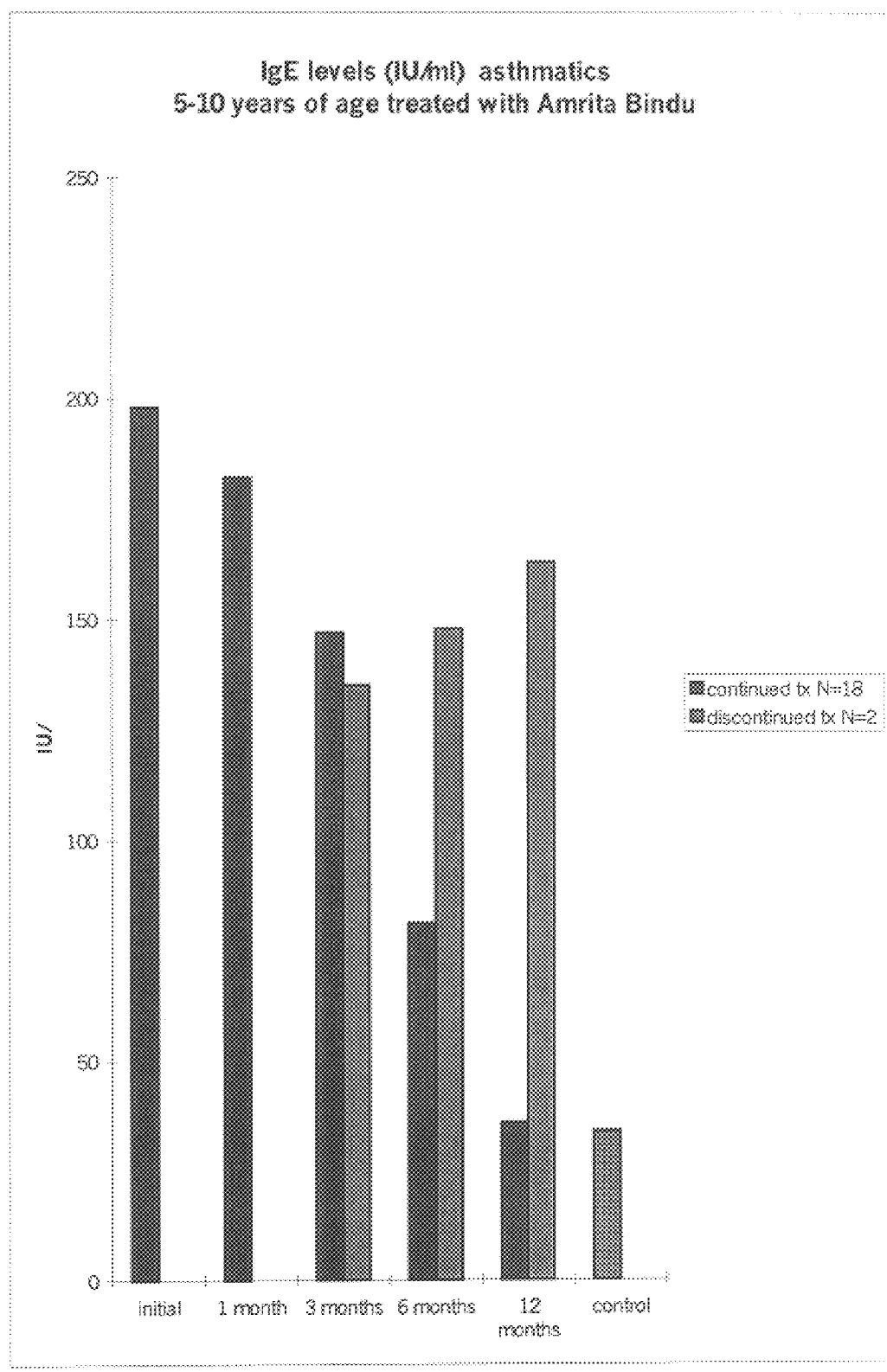
FIG. 1 is a graph, an explanation and a data chart containing information about serum IgE levels and the use of the present invention in asthmatic children 5–10 years of age.

An object of the present invention is to provide a clinically useful composition that stops IgE mediated reactions at the earliest stages. The inventors of the present invention have found after much research that the present composition which is capable of decreasing IgE levels can be used to treat mammals in whom IgE levels are abnormally increased thus treating the diseases associated with said IgE increase. This composition can be administered either prophylactically to prevent an allergic reaction or can be administered after the reaction has been ongoing even for many months to years since the composition can decrease the levels of IgE even though they have been elevated for some time. This composition is effective in lowering IgE levels and does so without side effects. Other aspects of the present invention will become evident upon reference to the following graphs and detailed description. To this end, certain references are listed herein for purpose of illustration and reference, and are incorporated herein by reference to their entirety.

DETAILED DESCRIPTION OF THE INVENTION

As mentioned above, this invention is generally directed to a composition that is shown to decrease and/or normalize elevated IgE levels and therefore have utility as an inhibiting agent of IgE, as well as the prevention and/or treatment of a number of conditions associated with increased IgE levels in warm-blooded animals, including humans.

As used herein, the term "conditions" includes diseases, injuries, disorders, indications and afflictions that are associated with IgE. Conditions "associated with IgE" are those conditions that result, either directly or indirectly from increased IgE levels. The term "treat" or "treatment" means that the symptoms associated with one or more conditions associated with elevated IgE are alleviated or reduced in severity or frequency, and the term "prevent" means that subsequent occurrence of such symptoms are avoided or the frequency between such occurrences is prolonged.

The composition used in accordance with the present invention is designated "Composition A." which is also known as Amerita Bindu. It is prepared as follows:

Step 1

500 grams of dried spikes of Tribulus terrestris L. are pulverized, soaked in 16 liters of water overnight, boiled for 4 hours and filtered. Filtrate is reduced to 2 liters by evaporation, cooled and stored to be used for the next step.

Step 2

Mix together the following:

500 grams of a mixture of chlorides of potassium and sodium, mixed with sulphate and carbonates of calcium and traces of aluminum, 250 grams of rock salt, 250 grams of bangle salt (made from the slag which is formed during the manufacture of glass when sodium carbonate and sand intermix in the heating process), 500 grams of an artificial salt prepared by fusing together a mixture of 40 kgs of sea salt, 500 gram of dried fruits of Terminalia chebula, 500 grams dried fruits of Phyllanthus embilica and 500 grams crude sodium carbonate, 100 grams of crude borax, and 400 grams of a salt made by burning the ash of a variety of woods including bamboos, soluble part of the ash is recrystalized from water. All of the forgoing is mixed together and ground for several hours along with a decoction of Tribulus terrestris. The dough obtained is wrapped in 5–6 leaves of Calatropis gigantean and dried. The dried packed salt mixture is transferred to an earthenware pot and closed with a close-fitting round flat dish which is sealed with clay. The pot is heated on an oven with smokeless coal as fuel for about 6 hours until the clay used to seal the pot appears baked and red colored. After cooling, the seal is broken and the fused salt mixture is pulverized and stored in a clean dry amber colored bottle. The yield of the salt mixture is 75% (w/w).

Step 3

100 grams each of dried ginger, pepper, dried berries of Piper longum Linn., root barks of Plumbago zeylanica and tubers of Cyperus rotundus are pulverized and to this is added 100 grams of the salt mixture obtained from Step 2 above. The ingredients are mixed to a homogeneous mass in a ball mill and removed and stored.

The constituents and the manufacturing process of Composition A as well as its ability to prevent the depletion of both endogenous as well as exogenous antioxidant defense mechanisms have been disclosed previously (Amrita Bindu-a salt-spice-herbal health food supplement for the prevention of nitrosamine induced depletion of antioxidants. K.R. Shanmugasundaram et al J. Ethnopharmacol. 42 (1994) 83–93); Amrita Bindu therapy in diabetic retinopathy: effect on antioxidant defenses and the disease process. Parthiban et al, Perfusion, Vol 9 pp280–283, 1996.) However, it should be understood that the novelty of this invention lies in the unexpected and surprising discovery of the ability of Composition A to lower serum IgE levels in mammals in need thereof unrelated to antioxidant defense mechanisms.

Accordingly, Composition A of this invention is believed effective in preventing or treating the above conditions due to its ability to inhibit or lower IgE. To this end, Composition A of this present invention may be used for pharmaceutical, prophylactic purposes and is administered to a warm-blooded mammal in an effective amount to achieve a desired result. In the case of pharmaceutical administration, an effective amount is a quantity sufficient to treat the symptoms of a condition and/or underlying condition itself. An effective amount in the context of prophylactic administration means an amount sufficient to avoid or delay the onset of a condition and its symptoms.

In a preferred embodiment, Composition A of the present invention is administered to a warm-blooded animal as a pharmaceutical or prophylactic composition in combination with at least one pharmaceutically or prophylactically acceptable carrier or diluent. Such compositions typically contain this composition in the amount ranging from 0.5% to 100%. Administration may be accomplished by systemic or topical application, with the preferred mode dependent upon the type and location of the condition to be treated. Frequency of administration may vary, and is typically accomplished by daily or twice daily administration.

Systemic administration may be achieved, for example, by injection (e.g., intramuscular, intravenous, subcutaneous or intradermal) or oral delivery of the composition to the warm-blooded animal. Suitable carriers and diluents for injection are known to those skilled in the art, and generally are in the form of an aqueous solutions containing appropriate buffers and preservatives. Oral delivery is generally accomplished by formulating the composition in a liquid or solid form, such as a tablet or capsule, by known formulation techniques.

Topical administration may be accomplished, for example, by formulating the composition as solution, cream, gel, ointment, powder, paste, gum or lozenge using techniques known to those skilled in the formulation field. As used herein, topical administration includes delivery of the composition to mucosal tissue of the mouth, nose and throat by, for example, spray or mist application, as well as to the vagina and rectum by, for example, suppository application.

In one embodiment of this invention by way of illustration and not by limitation, Composition A is administered to an animal in need thereof to lower IgE levels for the treatment or prevention of asthma. This may be accomplished by administering an effective amount of composition by any acceptable route of administration. The frequency of administration is preferably from about once a day to about three or four times a day and more preferably once or twice a day.

Examples illustrating the invention are provided below. They should be regarded as illustrating rather than limiting the invention.

EXAMPLE 1

Asthmatic children aged 5–10 were enrolled in this study. They all had been prescribed asthma medications (bronchodilators and steroid inhalers) and were to continue on their medications as long as needed. Serum IgE levels were done at baseline, after 1,3, 6 and 12 months into the study. Peak expiratory flow rates in L/min were measured at baseline, 6, and 12 months into the study. Use of asthma medications was monitored as well as potential side effects from the administration of the present composition. 500 mg of the composition was given daily in a single capsule.

| Serum IgE levels (IU/ml) | | |
| --- | --- | --- |
| | continued treatment 5–10 years of age N = 18 | discontinued treatment 5–10 years of age N = 2 |
| initial | 198 | 198 |
| 1 month | 182 | 182 |
| 3 months | 147 | 135 |
| 6 months | 81 | 148 |
| 12 months | 36 | 163 |
| control | 34 | |

As can be appreciated from the both the chart and the graph of the data in FIG. 1, serum IgE levels came down dramatically albeit slowly over the time period of the study. At month 3, all children had discontinued their standard asthma medications and continued on the composition only. The two patients who discontinued the composition after three months had an increase in serum IgE levels again and had to continue on their regular asthma medications.

| Peak Expiratory flow rate (L/min) | | |
| --- | --- | --- |
| | continued treatment 5–10 years of age N = 18 | discontinued treatment 5–10 years of age N = 2 |
| initial | 108 | 108 |
| 6 months | 136 | 120 |
| 12 months | 178 | 120 |
| control | 174 | |

Figure 2:
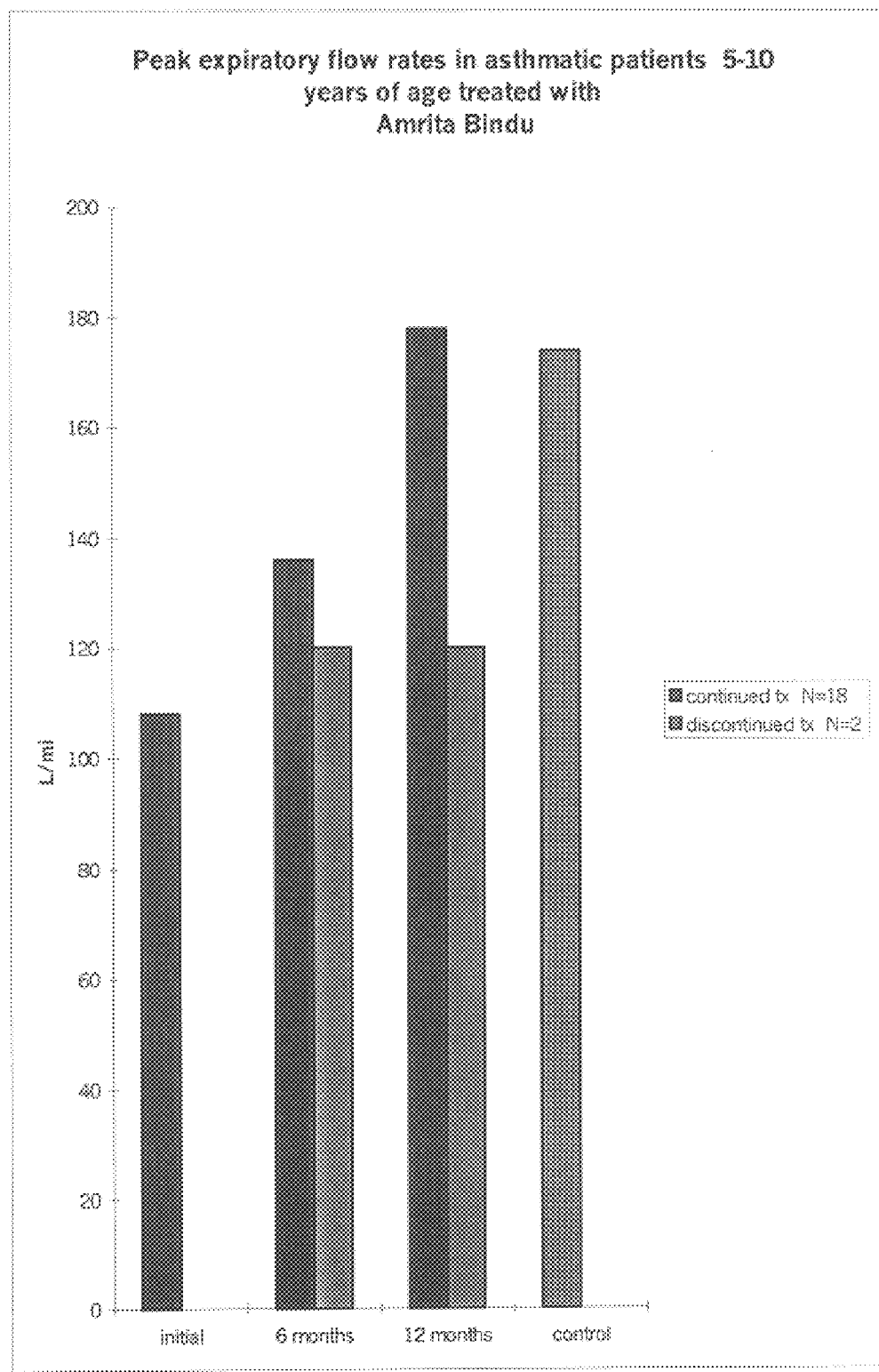
FIG. 2 is a graph, an explanation and a data chart containing information about peak expiratory flow rate and the use of the present invention in asthmatic children 5–10 years of age.

As can be appreciated from the both the chart and the graph of the data in FIG. 2, peak expiratory flow rates in L/min increased dramatically albeit slowly over the time period of the study and even surpassed those of the controls. The two patients who discontinued the composition after three months had a decrease in peak expiratory flow rates again and had to continue on their regular asthma medications.

EXAMPLE 2

Asthmatic children aged 11–20 were enrolled in this study. They all had been prescribed asthma medications (bronchodilators and steroid inhalers) and were to continue on their medications as long as needed. Serum IgE levels were done at baseline, after 1,3, 6 and 12 months into the study. Peak expiratory flow rates in L/min were measured at baseline, 6, and 12 months into the study. Use of asthma medications was monitored as well as potential side effects from the administration of the composition. Two capsules containing 500 mg of the composition were given daily.

| Serum IgE levels in IU/ml | | |
|---|---|---|
| | continued treatment 11–20 years of age N = 12 | discontinued treatment 11–20 years of age N = 3 |
| initial | 147 | 147 |
| 1 month | 133 | 133 |
| 3 months | 105 | 176 |
| 6 months | 72 | 203 |
| 12 months | 39 | 214 |
| control | 25 | |

Figure 3:
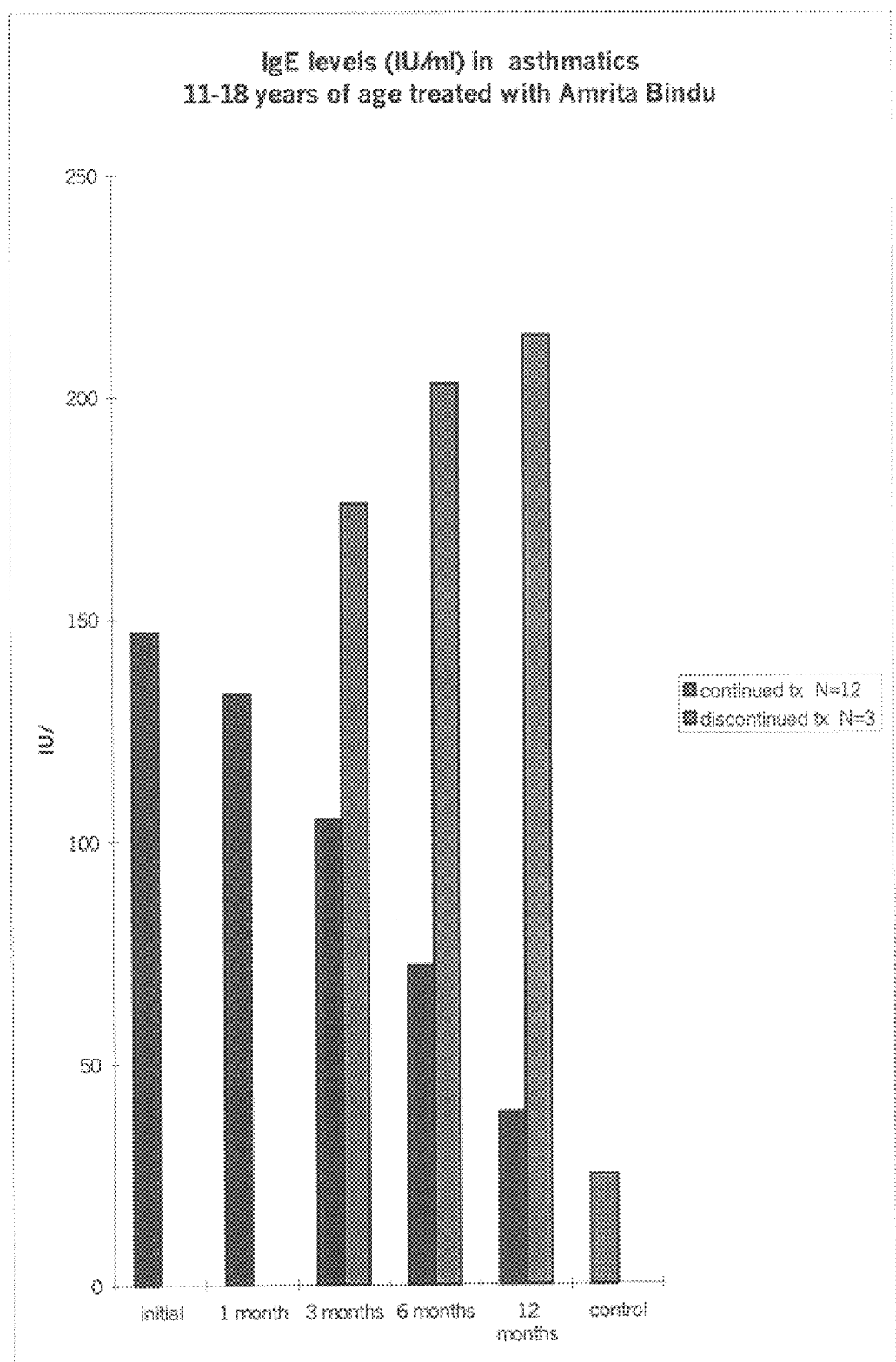
FIG. 3 is a graph, an explanation and a data chart containing information about serum IgE levels and the use of the present invention in asthmatic children 11–20 years of age.

As can be appreciated from the both the chart and the graph of the data in FIG. 3, serum IgE levels came down dramatically albeit slowly over the time period of the study. Serum IgE levels of the composition treated patients approached normal levels at the end of the study period. At month 6, all patients had discontinued their standard asthma medications and continued on the composition only. The three patients who discontinued the composition after three months had an increase in serum IgE levels again and had to continue on their regular asthma medications.

| Peak expiratory flow rates in L/min | | |
|---|---|---|
| | continued treatment 11–20 years of age N = 12 | discontinued treatment 11–20 years of age N = 3 |
| initial | 201 | |
| 6 months | 247 | 201 |

| -continued | | |
|---|---|---|
| Peak expiratory flow rates in L/min | | |
| | continued treatment 11–20 years of age N = 12 | discontinued treatment 11–20 years of age N = 3 |
| 12 months | 286 | 205 |
| control | 263 | |

Figure 4:
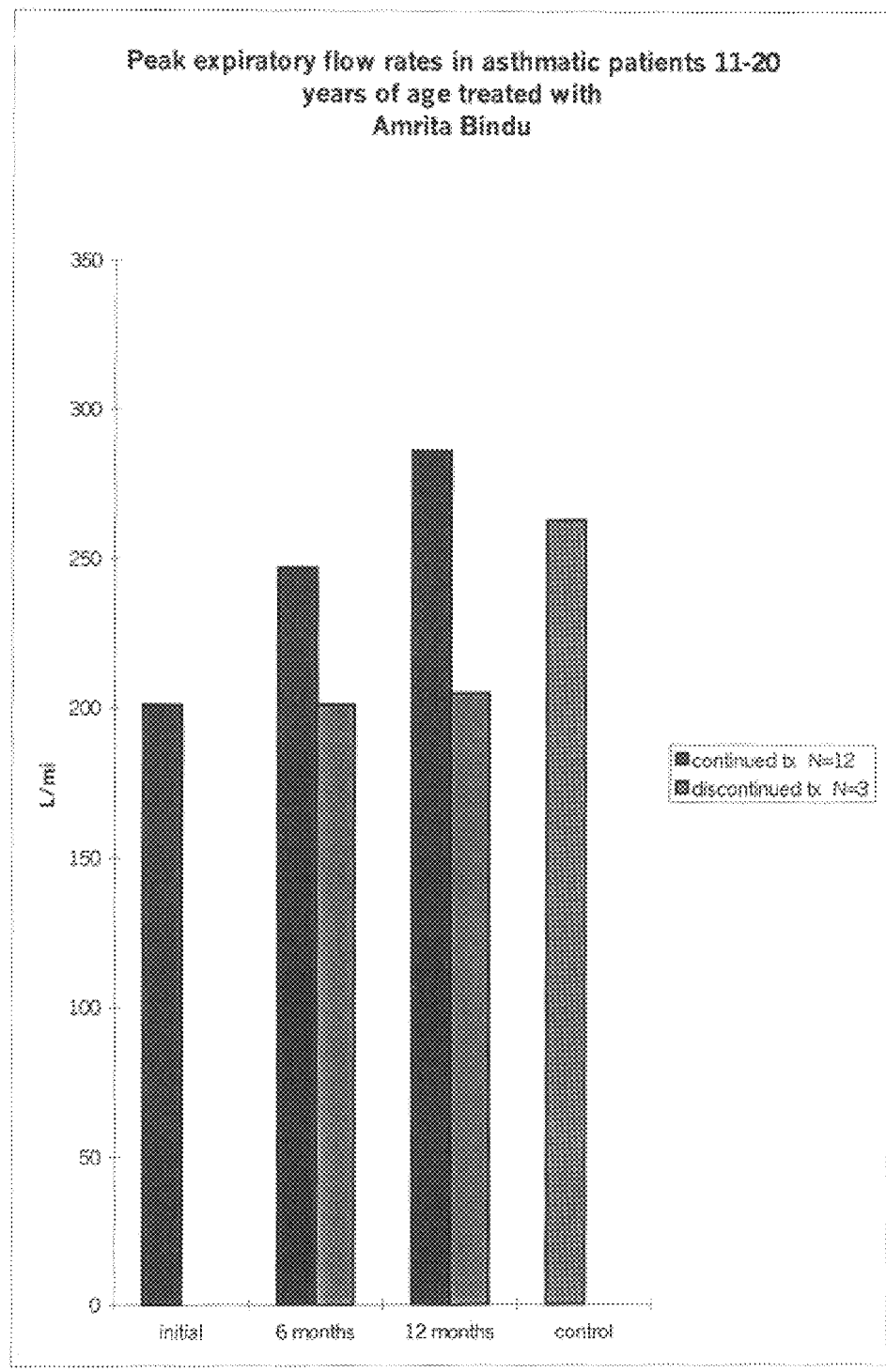
FIG. 4 is a graph, an explanation and a data chart containing information about peak expiratory flow rate and the use of the present invention in asthmatic children 11–20 years of age.

As can be appreciated from the both the chart and the graph of the data in FIG. 4, peak expiratory flow rates in L/min increased significantly albeit slowly over the time period of the study and even surpassed those of the controls. The three patients who discontinued the composition after three months had no increase in peak expiratory flow rates and had to continue on their regular asthma medications. There were no side effects noted from administration of the composition.

We claim:

1. A method of lowering elevated IgE levels in a mammal in need thereof comprising administering to said mammal, Amrita Bindu, an herbal-salt-spice mixture, in an amount effective to lower said serum IgE levels.

2. A method of lowering elevated serum IgE levels in a mammal in need thereof according to claim 1 for the treatment of conditions associated with elevated serum IgE levels wherein the condition is chosen from the group consisting of shock, allergy, atopy and asthma.

3. A method of lowering elevated serum IgE levels in a mammal in need thereof for the treatment of conditions associated with elevated serum IgE levels according to claim 1, whereby the Amrita Bindu is administered at a daily dosage of between 5 mg and 20 grams.

4. A method of lowering elevated serum IgE levels in a mammal in need thereof for the treatment of conditions associated with elevated serum IgE levels according to claim 1, whereby the Amrita Bindu is administered at a dosage of between 500 mg and 1 gram once or twice daily.

* * * * *